Figure 1:
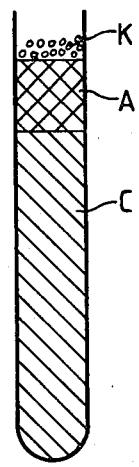

United States Patent [19]

Heimreid

[11] 4,379,849
[45] Apr. 12, 1983

[54] METHOD AND MEANS FOR THE EXAMINATION OF UNCOAGULATED BLOOD

[76] Inventor: Ken Heimreid, Brånanveien 44 B, 3940 Heistad, Norway

[21] Appl. No.: 191,818

[22] Filed: Sep. 26, 1980

[30] Foreign Application Priority Data

Oct. 4, 1979 [NO] Norway .................................. 793190

[51] Int. Cl.³ ...................... B01D 21/26; G01N 33/16
[52] U.S. Cl. ................................... 436/177; 210/516; 210/789; 422/72; 422/73; 422/101
[58] Field of Search .................. 23/230 B; 422/72, 68, 422/73, 101; 210/516, 789

[56] References Cited

U.S. PATENT DOCUMENTS 3,920,557 11/1975 Ayres ................................... 210/789
4,134,832 1/1979 Heimreid ........................... 422/73 X Primary Examiner—Michael S. Marcus Attorney, Agent, or Firm—Cushman, Darby & Cushman

[57] ABSTRACT

A method to facilitate the analysis of uncoagulated blood, for example freshly drawn blood or heparin blood, wherein the blood is filled into a test tube of plastic and a porous, elastic body in which one or more ballast element optionally are embedded, is placed in the upper layer of the blood and the blood is centrifuged such that the body in friction contact with the inner surface of the test tube is pressed through the blood, wherein the body or bodies are of glass or another suitable material with a surface whose characteristics correspond to those of glass, and where in addition there is used an overlying layer of small beads or other particles whose specific gravity is adapted in such a way that the beads after the centrifugation are embedded in the fibrin layer as reinforcement, and further wherein the two features may be combined by utilzing only the described small beads. A means for carrying out the method is also described.

5 Claims, 8 Drawing Figures

U.S. Patent  Apr. 12, 1983  4,379,849

METHOD AND MEANS FOR THE EXAMINATION OF UNCOAGULATED BLOOD

The present invention relates to a method and a means for facilitating the examination of uncoagulated blood, for example, freshly-drawn blood or heparin-added blood.

In particular, the invention pertains to an improvement on the method and the means described in Norwegian Pat. No. 137.663.

In order to obtain blood serum which is suitable for analysis or other further treatment, one has previously been forced to let the blood stand in test tubes for as long as 30 minutes to allow the blood to coagulate before being subjected to centrifugation. This procedure has two major drawbacks: The coagulation time required may cause an undesirable delay in the performance of necessary analyses, for example, in emergency situations; and the serum, following centrifugation, is not fibrin-free, and the red corpuscles are for the most part surrounded by fibrin as coagulant gel. This in turn results in a not-insignificant reduction in the volume of the total serum in the blood.

In the above-mentioned patent specification, a method is described wherein, during centrifugation, a porous body is pressed through uncoagulated blood, whereby a rapid activation of the total fibrinogen in the blood occurs, and the fibrinogen is converted into fibrin. The method can also be used with uncoagulated blood in which anticoagulants have been added if the porous body is impregnated with a suitable defibrinating substance. The formation of coagulant gel in the blood is thus entirely or partially prevented, depending on how quickly the activation process is initiated following the withdrawal of the blood sample. By initiating activation promptly following the withdrawal of the blood, therefore, one is enabled to liberate the total volume of serum in the blood.

In accordance with the patent, three strata are formed in the test tube by centrifugation, namely, a layer of fibrin, a fibrin-free layer of serum above the fibrin, and a fibrin-free layer consisting of red corpuscles below the fibrin.

Thus, according to the patent, one obtains a degree of separation between the red corpuscles at the bottom of the tube and the serum at the top.

A drawback of the patented method, however, is that it requires the use of centrifuge tubes made of glass or plastic tubes treated so as to provide them with a glass-like surface on the interior thereof, as it was not possible to obtain the necessary rapid activation with the plastic tubes.

Another disadvantage of the patent is that the intermediate fibrin layer so produced is not particularly firm, which imposes very stringent requirements for undisturbed transportation of the tube so as not to remingle its contents, and the transportation of such tubes from one department to another in the same institution or even from one institution to another is often necessary.

It is the object of the present invention to remedy these deficiencies. Thus, the invention relates to a method for facilitating examination of uncoagulated blood, for example, freshly-drawn blood or heparin-blood, where the blood is filled into a test tube and, optionally following a short pre-centrifugation, a body is placed in the upper layer of the blood, and the blood is thereafter centrifuged such that the body, in friction contact with the interior surface of the tube, is pressed through the blood, and the method of the invention is characterized by utilization of one or more body/bodies of glass or another suitable material having a surface whose characteristics correspond to those of glass, and by using, in addition to said body or bodies, an overlying layer of small beads or other suitable particles having a specific gravity so adapted that the beads find themselves embedded as reinforcement in the layer of fibrin following centrifugation, whereby the two features can also be combined by the utilization only of small beads or other particles of glass or of another suitable material whose surface characteristics correspond to those of glass, having a specific gravity so adapted that the beads find themselves embedded as reinforcement in the fibrin layer following centrifugation.

The invention also relates to a means for carrying out the method recited above, comprising a test tube and one or more bodies in which one or more ballast bodies are optionally embedded, and the means is characterized in that the body or bodies consist of glass or another suitable material having a surface whose characteristics correspond to those of glass, and that the means in addition comprises an overlying layer of small beads or other suitable particles whose specific gravity is so adapted that the beads find themselves embedded as reinforcement in the fibrin layer following centrifugation, whereby the two features can also be combined so as to comprise only the small beads or other particles of glass or of another suitable material whose surface characteristics correspond to those of glass, with a specific gravity so adapted that the beads find themselves embedded as reinforcement in the fibrin layer following centrifugation.

Owing to the fact that, in accordance with the invention, a body as described above is utilitzed, it is now possible to cease using the more expensive centrifuge tubes of glass, as one now obtains the same rapid activation and separation even with the use of plastic tubes.

Furthermore, as a result of the small beads or other suitable particles embedded therein, the fibrin layer separating the layer of serum and the layer of blood corpuscles becomes substantially reinforced such that the risk of a re-mixing of the blood components is greatly reduced during any necessary transportation of the centrifuge tube. Both of these factors represent significant advantages in relation to previous solutions.

Figure 2:
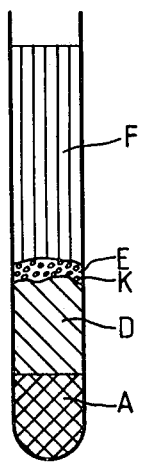
Figure 3:
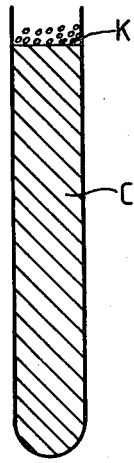
Figure 4:
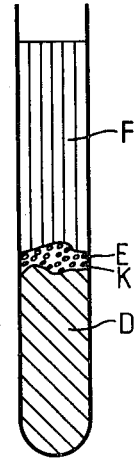
Figure 5:
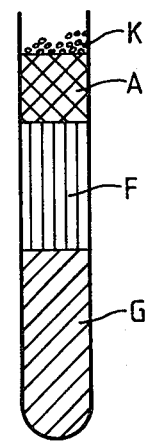
Figure 6:
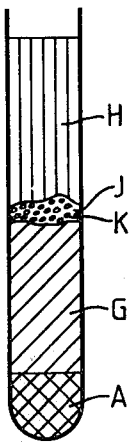
Figure 7:
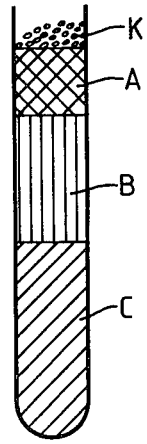
Figure 8:
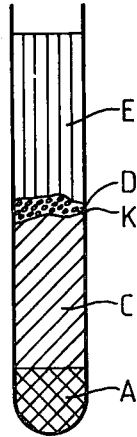

The invention will be elucidated further with reference to the accompanying drawings, where FIG. 1 is a schematic illustration showing a test tube containing uncoagulated whole blood, the elastic body and the particles, prior to centrifugation, FIG. 2 shows the test tube of FIG. 1 following centrifugation, FIGS. 3 and 4 show the same elements as FIGS. 1 and 2, but where only small beads or other suitable particles are employed, FIG. 5 is a schematic illustration showing citrate-blood prior to its second centrifugation, with the elastic body and the particles on top of the blood in the test tube, FIG. 6 shows the condition of the citrate-blood of FIG. 5 following the second centrifugation, FIG. 7 is a schematic illustration showing heparin-blood prior to its second centrifugation, with the body and beads on top of the blood in the test tube, and FIG. 8 shows the condition of the blood of FIG. 7 following the second centrifugation.

With reference to FIG. 1, the body A is placed in the uncoagulated, freshly-drawn whole blood C in a test tube, which is then placed in a centrifuge (not illustrated). Above this body, a layer of suitable particles having a specific gravity as described above is added. Alternately, as stated above, the use of said body can be omitted if one uses particles made of glass or whose surface corresponds to that of glass, having a specific gravity which is adapted such that the beads will become embedded as reinforcement in the fibrin layer following centrifugation. The two alternatives are shown in FIGS. 1 and 3, respectively.

During centrifugation, the body A will be pressed down through the blood toward the bottom of the test tube, so that, following centrifugation, one finds the body at the bottom of the tube, a stratum of fibrin-free red corpuscles D directly above it, a clump of fibrin E above this, and purified, fibrin-free serum F above the fibrin clump E, as shown in FIG. 2, while the particles K remain between the serum and the red corpuscles as reinforcement for the fibrin layer E, as shown in FIGS. 2 and 4.

Prior to the second centrifugation of citrate-blood, see FIG. 5, the body A, which has been impregnated with the defibrinating substance calcium chloride, and particles K, disposed above the body A, are placed into the plasma F, which as a result of the first centrifugation of the citrate-blood lies above the red corpuscles G. Following the second centrifugation, as shown in FIG. 6, the body will have been pressed down through the plasma F of FIG. 5, and through the red corpuscles G of FIG. 6, to the bottom of the test tube, while the fibrin has become separated as a concentrate, a clump J, resting on the surface of the red corpuscles G, and serum H has formed above the fibrin clump J. The fibrin is reinforced by the particles K. The body A is in the bottom of the test tube.

Prior to the second centrifugation of heparin-blood, see FIG. 7, the body A which is impregnated with protamine sulphate, together with the overlying particles K, are placed in the plasma B which, as a result of the first centrifugation, lies above the red corpuscles C. Following the second centrifugation see FIG. 8, the body will have been pressed through the plasma B of FIG. 7, and through the red blood corpuscles C of FIG. 8, to the bottom of the test tube, while the fibrin has become separated as a concentrated clump D on the surface of the red corpuscles C and separates the latter from the serum E which has now formed above the fibrin clump D. The fibrin is reinforced by the particles K. The body A is at the bottom of the test tube.

It will be clear to the skilled practitioner that the technique described above in connection with FIGS. 3 and 4 can also be adapted to the two cases described in the preceding two paragraphs.

Having described my invention, I claim:

1. A method for facilitating the examination of uncoagulated blood comprising (1) filling the blood into a plastic test tube, (2) placing in the upper layer of the blood one or more bodies of glass or another suitable material with a surface whose characteristics correspond to glass, (3) placing above said one or more bodies an overlying layer of small beads or other suitable particles whose specific gravity is such that the small beads or other suitable particles become embedded as reinforcement in the fibrin layer following centrifugation and (4) centrifuging the blood while said body or bodies is in friction contact with the interior surface of the tube and pressing said body or bodies through the blood during said centrifugation.

2. A method according to claim 1 wherein the blood is freshly-drawn blood or heparin-blood.

3. A method according to claim 1 comprising carrying out a brief pre-centrifugation of the blood in the test tube prior to placing the body in the upper layer of the blood.

4. In a device for separating of uncoagulated blood into components comprising in combination a test tube of plastic and a porous elastic body or bodies of glass or another suitable material having a surface whose characteristics correspond to those of glass and which is insertable into said test tube, the improvement comprising a plurality of small beads or other suitable particles insertable into said tube above said porous elastic body and having a specific gravity which is so adapted that the beads or other particles find themselves embedded as reinforcement in the fibrin layer when blood is centrifuged in the test tube.

5. A device according to claim 4 wherein at least one ballast element embedded in said porous elastic body.

* * * * *